US00PP29815P2

(12) United States Plant Patent
Baba et al.

(10) Patent No.: US PP29,815 P2
(45) Date of Patent: Nov. 6, 2018

(54) SHIITAKE MUSHROOM PLANT NAMED 'FFT-52'

(50) Latin Name: ***Lentinus edodes* (Berk.) Sing.**
Varietal Denomination: FFT-52

(71) Applicant: FFT USA CORPORATION, Torrance, CA (US)

(72) Inventors: Takahiko Baba, Agatsuma-gun (JP); Okura Masuda, Agatsuma-gun (JP); Takahisa Mori, Agatsuma-gun (JP); Sean M. E. Earing, Torrance, CA (US)

(73) Assignee: FFT USA CORPORATION, Torrance, CA (US)

( * ) Notice: Subject to any disclaimer, the term of this patent is extended or adjusted under 35 U.S.C. 154(b) by 0 days.

(21) Appl. No.: 15/731,528

(22) Filed: Jun. 22, 2017

(51) Int. Cl.
*A01H 5/00* (2018.01)

(52) U.S. Cl.
USPC ..... Plt./394

(58) Field of Classification Search
USPC ..... Plt./394
See application file for complete search history.

(56) References Cited

PUBLICATIONS

Yonekura et al., "JMS KV-92", Ministry of Agriculture, Forestry and Fisheries of Japan, Jan. 16, 2002, w/English Abstract, cited in Specification (2 pages).
Inoue, "Hokken 600GO", Ministry of Agriculture, Forestry and Fisheries of Japan, Nov. 5, 1988, w/English Abstract, cited in Specification (2 pages).
Yamauchi et al., "KB-2010GO", Ministry of Agriculture, Forestry and Fisheries of Japan, Mar. 30, 2000, w/English Abstract, cited in Specification (2 pages).

*Primary Examiner* — Annette H Para
(74) *Attorney, Agent, or Firm* — Westerman, Hattori, Daniels & Adrian, LLP

(57) ABSTRACT

The inventive variety of shiitake mushroom plant named 'FFT-52' is morphologically characterized by a greater pileus diameter and a greater pileus thickness. Further, 'FFT-52' ensures a higher crop yield and an easier harvesting operation because it can be easily harvested manually without the use of a harvesting device. In addition, 'FFT-52' is highly resistant to a high-temperature load.

28 Drawing Sheets

Latin name of the genus and species of the plant claimed: *Lentinus edodes* (Berk.) Sing.

Variety denomination: Shiitake mushroom plant 'FFT-52'.

BACKGROUND OF THE INVENTION

The present invention relates to a new and distinct variety of shiitake mushroom plant named 'FFT-52' which is characterized by a greater pileus diameter, a greater pileus thickness, a higher crop yield, an easier harvesting operation, and a higher resistance to a high-temperature load.

The claimed 'FFT-52' is a variety of shiitake mushroom produced by crossbreeding Japanese registered shiitake mushroom varieties 'KB-2010' (hereinafter referred to simply as 'KB-2010') (Registration No. 8118) and 'JMS KV-92' (hereinafter referred to simply as 'KV-92') (Registration No. 9781) and further crossbreeding the resulting variety 'KBT-1809' and another shiitake mushroom variety 'KBT-304' (see FIG. 1). More specifically, 'FFT-52' was produced through the following crossbreeding and cultivating process:

(1) In November 2006, dikaryotic mycelia produced by crossbreeding single-spore-derived monokaryotic mycelia of 'KB-2010' and 'KV-92' were allowed to grow into a colony, and a strain superior in mycelial growth and colony condition was selected from the colony.

(2) From December 2006 to July 2008, a cultivation test was performed by cultivating the selected strain in a fungal bed, and a strain superior in fruit body shape and crop yield was selected and named 'KBT-1809'.

(3) In December 2010, dikaryotic mycelia produced by crossbreeding monokaryotic mycelia of 'KBT-1809' and 'KBT-304 (stock strain)' were allowed to grow into a colony, and a strain superior in mycelial growth and colony condition was selected from the colony.

(4) From February 2011 to December 2012, a cultivation test was performed by cultivating the selected strain in a fungal bed, and a strain superior in fruit body shape and crop yield was selected and named 'FFT-52' (inventive variety).

(5) From 2013 to 2014, an extensive cultivation test was performed. In 2014, it was confirmed that 'FFT-52' has stable characteristics.

An asexually reproduced clone of the inventive variety is identical to the original inventive variety in all distinguishing characteristics.

SUMMARY OF THE INVENTION

Noticeable characteristics of the inventive variety 'FFT-52' are as follows:

1. 'FFT-52' has a greater pileus diameter, a greater pileus thickness and a greater fruit body weight (shiitake mushroom weight) than existing varieties.

2. 'FFT-52' ensures a higher crop yield and an easier harvesting operation than the existing varieties because it can be easily harvested manually without the use of a harvesting device.
3. 'FFT-52' is highly resistant to a high-temperature load and, even if being cultivated in a higher temperature environment, is less susceptible to growth inhibition than the existing varieties.

BRIEF DESCRIPTION OF THE DRAWINGS

FIG. 1 is a genealogical chart for 'FFT-52'.

FIG. 2 is a diagram showing designations of parts of a fruit body, in which i designates a pileus, ii designates a hymenophore, iii designates a stipe, and iv designates scales.

FIG. 3 is a diagram showing dimensional designations of the fruit body, in which I designates the diameter of the pileus, II designates the thickness of the pileus, III designates the width of the hymenophore, IV designates the length of the stipe, and V designates the thickness of the stipe.

FIGS. 4A to 4C are images to be used as references for determination of scale location.

FIGS. 5A to 5C are photographs to be used as references for determination of scale size.

FIGS. 6A and 6B are photographs to be used as references for determination of a gill configuration of the hymenophore.

FIGS. 7A and 7B are images to be used as references for determination of hymenophore density.

FIG. 8 is a photograph to be used as a reference for determining whether the stipe is classified as "colorless" or "colored".

FIG. 9 is a photograph showing a top view of a fruit body of 'FFT-52'.

FIG. 10 is a photograph showing a side view of the fruit body of 'FFT-52'.

FIG. 11 is a photograph showing a bottom view of the fruit body of 'FFT-52'.

FIG. 12 is a photograph showing a sectional view of the fruit body of 'FFT-52'.

FIG. 13 is a photograph showing a top view of a fruit body of a comparative variety 'KA-1001' (hereinafter referred to simply as 'KA-1001').

FIG. 14 is a photograph showing a side view of the fruit body of 'KA-1001'.

FIG. 15 is a photograph showing a top view of a fruit body of a comparative variety 'Hokken 600' (hereinafter referred to simply as 'H600').

FIG. 16 is a photograph showing a side view of the fruit body of 'H600'.

FIG. 17 is a photograph showing sectional views of fruit bodies of 'FFT-52' 'KA-1001' and 'H600' in comparison.

FIG. 18 is a graph showing the crop yields of 'FFT-52' 'KA-1001' and 'H600' in a cultivation test.

FIG. 19 is a photograph showing the cultivation of 'FFT-52'.

FIG. 20 is a photograph showing the harvesting of 'FFT-52'.

FIG. 21 is a photograph showing a sectional view of a fungal bed of 'KB-2010' suffering from high-temperature damage on the 40th day of cultivation.

FIG. 22 is a photograph showing a sectional view of a fungal bed of 'FFT-52' on the 40th day of cultivation.

FIGS. 23A and 23B are photographs showing a top view and a bottom view, respectively, of dual culture of 'FFT-52'.

FIGS. 24A and 24B are photographs showing a top view and a bottom view, respectively, of dual culture of 'FFT-52' and 'KA-1001'.

FIGS. 25A and 25B are photographs showing a top view and a bottom view, respectively, of dual culture of 'FFT-52' and 'H600'.

FIGS. 26A and 26B are photographs showing a top view and a bottom view, respectively, of dual culture of 'FFT-52' and 'KB-2010'.

FIGS. 27A and 27B are photographs showing a top view and a bottom view, respectively, of dual culture of 'FFT-52' and 'KV-92'.

FIGS. 28A and 28B are photographs showing a top view and a bottom view, respectively, of dual culture of 'FFT-52' and 'JMS 9K-4' (hereinafter referred to simply as '9K-4').

FIGS. 29A and 29B are photographs showing a top view and a bottom view, respectively, of dual culture of 'FFT-52' and 'Mori XR1' (hereinafter referred to simply as 'XR1').

FIGS. 30A and 30B are photographs showing a top view and a bottom view, respectively, of dual culture of 'FFT-52' and 'Mori XR18' (hereinafter referred to simply as 'XR18').

FIGS. 31A and 31B are photographs showing a top view and a bottom view, respectively, of dual culture of 'FFT-52' and 'Mori Tomutomu' (hereinafter referred to simply as 'ML8').

FIGS. 32A and 32B are photographs showing a top view and a bottom view, respectively, of dual culture of 'FFT-52' and 'Akiyama A-567' (hereinafter referred to simply as 'A-567').

FIGS. 33A and 33B are photographs showing a top view and a bottom view, respectively, of dual culture of 'FFT-52' and 'KINKO 241' (hereinafter referred to simply as 'K241').

FIGS. 34A and 34B are photographs showing a top view and a bottom view, respectively, of dual culture of 'FFT-52' and 'Hokken 607' (hereinafter referred to simply as 'H607').

FIGS. 35A and 35B are photographs showing a top view and a bottom view, respectively, of dual culture of 'FFT-52' and 'KX-S055' (hereinafter referred to simply as 'KX-S055').

FIG. 36 is a Table describing observations of the shape of the pileus.

FIG. 37 is a Table describing observations of hymenophores.

FIG. 38 is a Table describing observations and evaluations of stipes.

DETAILED BOTANICAL DESCRIPTION

There are two shiitake mushroom cultivation methods, i.e., a log cultivation method and a fungal bed cultivation method. The fungal bed cultivation method is commonly used in the world.

In the fungal bed cultivation method, a shiitake mushroom spawn is generally inoculated in a culture medium contained in a culture bag having a ventilation filter, and cultured for a predetermined period. Thus, a fungal bed is prepared. Thereafter, the fungal bed is cultivated to produce fruit bodies.

There are mainly two fungal bed preparation methods. In a first method, which requires light, a shiitake mushroom spawn is cultured in a culture bag for about 70 to about 150 days. In a second method, a culture medium in which mycelia are fully propagated is taken out of a culture bag after about 40 days of culturing and the mycelia in the culture medium are further cultured at a proper humidity in a water sprinkling environment for about 60 days.

In the first fungal bed preparation method, the resulting fungal bed has a relatively soft brown coating layer formed on its surface, and when the first fruit body is developed immediately after the bag is torn, then the fungal bed rests. Thereafter, development of the second fruit body is promoted through fruiting stimulation by water soaking or water injection. Then, a cycle including the fruiting stimulation, the development and the resting is repeated, whereby fruit bodies are intensively developed in a limited fruiting period.

In the second fungal bed preparation method, on the other hand, the resulting fungal bed has a harder brown coating layer formed on its surface than in the first fungal bed preparation method. Therefore, water is sprinkled over the fungal bed for a short period of time every day without performing the fruiting stimulation by the water soaking or the water injection, whereby fruit bodies are sporadically developed by stimulation induced by temperature variation based on daily temperature difference every consecutive day during the entire cultivation period.

The inventive variety 'FFT-52' has been developed for the fungal bed cultivation which permits the development of fruit bodies through short-period culture, and is adaptable to the first and second fungal bed preparation methods.

The features of 'FFT-52' will hereinafter be described.

[Morphological Characteristics]

The morphological characteristics of 'FFT-52' will be described in comparison with existing varieties, i.e., a variety 'KA-1001' applied for plant variety registration in Japan (Application No. 27359) and a Japanese registered variety 'H600' (Registration No. 1791).

'FFT-52' 'KA-1001' and 'H600' were cultivated in the following manner by the fungal bed cultivation method, and the resulting fruit bodies were measured and observed for determination of morphological characteristics thereof.

The fruit bodies of these varieties for the comparison test were cultivated in Gunma, Japan from April 2016 to January 2017.

A polyethylene culture bag having a respiration filter for mycelia was used in culture for preparation of each fungal bed. Culture medium was prepared by mixing sawdust of broadleaved trees including not less than 70 weight % of Quercus serrata, rice bran and wheat bran in a mixing weight ratio of 8:1:1 and adjusting the water content of the resulting mixture at 60 weight %. The culture bag was filled with 1.1 kg of the culture medium, which was in turn sterilized at 121° C. for 90 minutes by a high-pressure steam sterilization method. Fungal spawns of the aforementioned varieties were each inoculated in the sterilized culture medium, and cultured in a culture chamber conditioned at a culturing temperature of 20° C. to 23° C. for 40 days. Thereafter, the culture medium in which mycelia were fully propagated was taken out of the bag, and the mycelia in the culture medium was further cultured for 60 days. Thus, a fungal bed was prepared. Then, a plurality of such fungal beds of the aforementioned varieties were placed on shelf boards of a multi-tier shelf in a cultivation house, and cultivated to allow for the development of fruit bodies. For the cultivation, the cultivation house was maintained at a higher temperature (20° C. to 22° C.) for a higher-temperature period of 9 hours per day and at a lower temperature (9° C. to 11° C.) for a lower-temperature period of 9 hours per day by utilizing an air conditioner, and water was sprinkled for 0.5 to 2 hours per day. Natural light was utilized to maintain the illuminance at 200 to 500 lux during the daytime in the cultivation house.

In the full fruiting period, 100 fruit bodies with their pilei in an 80- to 90-percent open state (with their back veils partly broken) were picked up at random. Then, the dimensions of each of the fruit bodies were measured, and the pileus shape, the pileus color and the pileus flesh texture of each of the fruit bodies, and the scales, the hymenophore and the stipe of each of the fruit bodies were observed (see FIGS. 2 and 3). The observation and the measurement for the test were performed based on Research Report on Plant Variety Characteristic Classification, Mushroom (shiitake), 1994-1995, Japan.

The results of the measurements of the fruit bodies' dimensions are shown below in Table 1. In Table 1, the measured dimensions are each shown in the form of average±standard deviation, and the figures with ** are significant at significance level of 1%.

TABLE 1

Measurement of dimensions of fruit body)

| Dimensions of fruit body | FFT-52 | KA-1001 | H600 |
|---|---|---|---|
| Diameter of (m pileusm) | 85.1 ± 14.2** | 71.2 ± 12.7 | 65.6 ± 7.9 |
| Thickness of pileus (nm) | 18.1 ± 2.4** | 15.8 ± 2.3 | 14.6 ± 2.3 |
| Width of gills (mm) | 3.2 ± 0.8 | 2.4 ± 0.8 | 4 ± 0.9 |
| Length of stipe (mm) | 47.9 ± 7 | 47.1 ± 7 | 53.5 ± 9.1 |
| Pileus diameter/ stipe length | 1.8 ± 0.3 | 1.5 ± 0.2 | 1.3 ± 0.2 |
| Diameter of stipe (mm) | 14.9 ± 2.4 | 14.3 ± 2.4 | 11.5 ± 2.1 |
| Pileus diameter/ stipe diameter | 5.8 ± 1 | 5.1 ± 1.1 | 5.9 ± 1.4 |
| Wet weight (g) | 87.1 ± 40.1** | 43.6 ± 18.4 | 30 ± 7 |
| Absolute dry weight (g) | 7.9 ± 3.4** | 4.2 ± 1.9 | 2.8 ± 0.7 |
| Dry weight percentage (%) | 9.3 ± 1 | 9.6 ± 1.4 | 9.4 ± 1.3 |
| Average dry weight (g) (with moisture content of 8%) | 8.6 ± 3.7** | 4.6 ± 2 | 3 ± 0.8 |
| Crop yield (kg) (8%) (Dry weight/100 kg fungal bed) | 6.7 | 5.4 | 5 |

**$p < 0.01$

The inventive variety 'FFT-52' was significantly greater in pileus diameter and pileus thickness than the existing varieties 'KA-1001' and 'H600'. Since these varieties had substantially the same stipe length, 'FFT-52' had the highest ratio of the pileus diameter to the stipe length. That is, 'FFT-52' had substantially the same stipe length and stipe thickness as the comparative variety 'KA-1001' and the stipe thickness of 'FFT-52' was greater than that of the comparative variety 'H600'. The pileus of 'FFT-52' was apparently larger and thicker than those of 'KA-1001' and 'H600'. Thus, 'FFT-52' was a shiitake mushroom having a greater size pileus.

Further, 'FFT-52' was significantly greater in wet fruit body weight, absolute dry fruit body weight and average dry fruit body weight than 'KA-1001' and 'H600'.

'FFT-52' was overwhelmingly greater in individual fruit body weight as well as pileus diameter and pileus thickness than 'KA-1001' and 'H600' and, when being held on hand, exhibited a massive feeling.

Subsequently, the shape of each of the fruit bodies was visually observed. The results of the observation are shown in FIG. 36.

The pileus of 'FFT-52' was mainly flat as viewed from lateral side, and relatively thick from its center to its periphery as viewed in section. The pileus of 'KA-1001' was mainly flat as viewed from lateral side, and progressively thinner in a direction from its center to its periphery as viewed in section. The pileus of 'H600' was mainly convex as viewed from lateral side, and thinner in a direction from its center to its periphery as viewed in section.

Further, the color of the pileus of each of the fruit bodies was observed.

The color designations herein used are based on The Colour Chart specified by The Royal Horticultural Society (The Royal Horticultural Society (R.H.S.) London, Sixth Edition (2015)).

TABLE 2

(Observation of color of pileus)

| Color | RHS No. | FHT-52 | KA-1001 | H600 |
|---|---|---|---|---|
| Dark greyish reddish brown | 200A | 14 | 3 | 12 |
| Dark greyish yellowish brown | N200A | 2 | 1 | 7 |
| Greyish reddish brown | 200B | 18 | 1 | 41 |
| Greyish brown | 166A | 2 | 1 | 3 |
| Moderate brown | 165A<br>200C<br>200D | 63 | 85 | 37 |
| Moderate yellowish brown | N199C | 0 | 1 | 0 |
| Strong yellowish brown | N199D | 0 | 2 | 0 |
| Moderate reddish brown | 175A<br>166B | 1 | 2 | 0 |
| Brownish orange | N167A<br>N167B | 0 | 4 | 0 |

The color of the upper surface of the pileus of 'FFT-52' was mainly moderate brown (RHS 165A, 200C, 200D). The color of the upper surface of the pileus of 'KA-1001' was mainly moderate brown (RHS 165A, 200C, 200D). The color of the upper surface of the pileus of 'H600' was mainly greyish reddish brown (RHS 200B).

Further, 'FFT-52' 'KA-1001' and 'H600' were each evaluated for the flesh texture of the pileus of the fruit body. For evaluation, the hardness of the pileus was determined by pinching the pileus with fingers. The flesh texture of the pileus was classified as "soft" when the pileus had a lower hardness than the pileus of Japanese registered variety 'MORI 440' (Registration No. 506), classified as "intermediate" when the pileus had substantially the same hardness as the pileus of 'MORI 440', or classified as "hard" when the pileus had substantially the same hardness as the pileus of Japanese registered variety 'KINKO 610' (Registration No. 821) or 'MORI 252' (Registration No. 193).

TABLE 3

(Evaluation for flesh texture of pileus)

| Flesh texture of pileus | FFT-52 | KA-1001 | H600 |
|---|---|---|---|
| Soft | 0 | 8 | 82 |
| Intermediate (Equivalent to MORI 440) | 18 | 54 | 16 |

TABLE 3-continued (Evaluation for flesh texture of pileus)

| Flesh texture of pileus | FFT-52 | KA-1001 | H600 |
|---|---|---|---|
| Hard (Equivalent to KINKO 610 or MORI 252) | 82 | 38 | 2 |

The pileus of 'FFT-52' mainly had a hard flesh texture. Further, the pileus of 'KA-1001' mainly had an intermediate flesh texture, and the pileus of 'H600' mainly had a soft flesh texture.

Scales of the pileus of each of the fruit bodies were visually observed. The scale location was classified as "entire area" when the scales were present over the entire upper surface of the pileus as shown in FIG. 4A, classified as "peripheral area" when the scales were present on the peripheral area of the pileus as shown in FIG. 4B, or classified as "none" when no scale was present on the pileus as shown in FIG. 4C. The scale size was classified as "small" when the scales each had a smaller size as shown in FIG. 5A, classified as "intermediate" when the scales each had an intermediate size as shown in FIG. 5B, or classified as "large" when the scales each had a larger size as shown in FIG. 5C. The scale color was classified as "colorless" when the scales were yellowish white (RHS NN155A) or classified as "colored" when the scales were colored other than white. The results are shown below in Table 4.

TABLE 4

(Observation of scales)

| | FFT-52 | KA-1001 | H600 |
|---|---|---|---|
| Scale location | | | |
| Entire area | 91 | 98 | 80 |
| Peripheral area | 9 | 2 | 20 |
| None | 0 | 0 | 0 |
| Scale size | | | |
| Small | 46 | 5 | 19 |
| Intermediate | 42 | 34 | 38 |
| Large | 12 | 61 | 43 |
| Scale color | | | |
| Colorless | 100 | 100 | 100 |
| Colored | 0 | 0 | 0 |

The scales of 'FFT-52' were mostly small, while the scales of 'KA-1001' and the scales of 'H600' were mostly large.

The hymenophore of each of the fruit bodies was visually observed. The gill configuration of the hymenophore was classified as "normal" when the gills of the hymenophore were straight as shown in FIG. 6A, or classified as "wavy" when the gills of the hymenophore were wavy as shown in FIG. 6B. The density of the hymenophore was classified as "sparse" when the hymenophore had a lower density as shown in FIG. 7A, classified as "dense" when the hymenophore had a higher density as shown in FIG. 7B, or classified as "intermediate" when the hymenophore had an intermediate density between the densities shown in FIGS. 7A and 7B. The density of the hymenophore of the pileus shown in FIG. 6A is intermediate. The results are shown below in FIG. 37.

The hymenophore of 'FFT-52' mainly had a triangular shape apart from the stipe and an intermediate density, and was yellowish white (RHS NN155A). The hymenophores of 'KA-1001' and 'H600' each mainly had a triangular shape apart from the stipe and an intermediate density, and were yellowish white (RHS NN155A).

The stipe of each of the fruit bodies was visually observed. The flesh texture of the stipe was defined by the hardness of the stipe determined by pinching the stipe with fingers. The flesh texture of the stipe was classified as "soft" when the stipe had substantially the same hardness as the stipe of Japanese registered variety 'JMS7H-3' (Registration No. 503), or classified as "hard" when the stipe had substantially the same hardness as the stipe of Japanese registered variety 'KINKO 535' (Registration No. 98). The color of the stipe was classified as "colorless" when the stipe entirely had a color between yellowish white (RHS NN155A) and pale yellow (RHS 158B), or classified as "colored" when the stipe had a lower one third portion colored moderate brown (RHS 165A) to greyish brown (RHS 166A) (see FIG. 8). The results are shown below in FIG. 38.

The stipe of 'FFT-52' mainly had an upwardly enlarged shape and a hard flesh texture, and was colorless. The stipe of 'KA-1001' mainly had an upwardly enlarged shape and an intermediate flesh texture, and was colorless. The stipe of 'H600' mainly had a barrel shape and an intermediate flesh texture, and was colored.

The results of the measurement and the observation indicate that the inventive variety 'FFT-52' is easily distinguishable in morphological characteristics from the existing varieties in the cultivation process (see FIGS. 9 to 17).

'FFT-52' is moderately chewy like chicken breast meat, and is excellent in taste and eating texture.

[Harvesting Characteristics]

Next, the harvesting characteristics of 'FFT-52' will be described. 'KA-1001' and 'H600' were used as comparative varieties for comparison of harvesting characteristics.

Fungal beds of 'FFT-52' 'KA-1001' and 'H600' were prepared by the same fungal bed preparation method as employed for the determination of the morphological characteristics, and then cultivated under the same conditions. The crop yields are shown below in Table 5 (see FIG. 18). Since fruit bodies each having a wet weight of not greater than 5 g cannot be easily distributed as they are in the market, the data of such fruit bodies is excluded from the harvest data.

The crop yields shown below are each defined as an average crop yield for 60 to 80 fungal beds used for the cultivation. The cultivation period was 120 days, and the crop yields were measured once every 30 days.

TABLE 5

(Crop yields of 'FFT-52' 'KA-1001' and 'H600')

| Strain name | Cultivation period | 30 days | 60 days | 90 days |
|---|---|---|---|---|
| FFT-52 | Crop yield (g) per month | 149.5 | 354.8 | 147.9 |
| | Cumulative crop yield (g) | 149.5 | 504.2 | 652.1 |
| KA-1001 | Crop yield (g) per month | 193.9 | 139.6 | 150.5 |
| | Cumulative crop yield (g) | 193.9 | 333.5 | 484.0 |
| H600 | Crop yield (g) per month | 68.2 | 135.5 | 187.8 |
| | Cumulative crop yield (g) | 68.2 | 203.7 | 391.4 |

TABLE 5-continued (Crop yields of 'FFT-52' 'KA-1001' and 'H600')

| Strain name | Cultivation period | 120 days | Total |
|---|---|---|---|
| FFT-52 | Crop yield (g) per month | 76.1 | 728.2 |
| | Cumulative crop yield (g) | 728.2 | — |
| KA-1001 | Crop yield (g) per month | 82.1 | 566.1 |
| | Cumulative crop yield (g) | 566.1 | — |
| H600 | Crop yield (g) per month | 151 | 542.5 |
| | Cumulative crop yield (g) | 542.5 | — |

'FFT-52' yielded 728.2 g of fruit bodies per bag of 1.1 kg fungal bed (see FIG. 19). In contrast, 'KA-1001' yielded 566.1 g of fruit bodies per bag of 1.1 kg fungal bed, and 'H600' yielded 542.5 g of fruit bodies per bag of 1.1 kg fungal bed. Thus, 'FFT-52' had a higher crop yield than the existing varieties.

Further, 'FFT-52' yielded an average of 16.6 fruit bodies per bag of fungal bed. 'KA-1001' yielded an average of 12.8 fruit bodies per bag of fungal bed, and 'H600' yielded an average of 24.2 fruit bodies per bag of fungal bed.

This means that 'FFT-52' yielded a greater number of greater-weight fruit bodies per bag of fungal bed than 'KA-1001'. Furthermore, 'FFT-52' yielded a smaller number of greater-weight fruit bodies per bag of fungal bed than 'H600'.

Thus, 'FFT-52' ensures a higher crop yield.

Further, the fruit bodies of 'FFT-52' each had a smaller stipe base, and their underground mycelia were present in a shallow surface portion of the fugal bed. Therefore, the fruit bodies of 'FFT-52' were easily manually harvested without the use of a harvesting device such as scissors (see FIG. 20).

[High-Temperature Load Resistance Characteristics]

Next, the high-temperature load resistance characteristics of 'FFT-52' will be described. 'KB-2010' was used as a comparative variety for comparison of the high-temperature load resistance characteristics. The following evaluation method was employed.

Fungal beds were prepared by the same fungal bed preparation method as employed for the determination of the morphological characteristics. More specifically, fungal spawns of the aforementioned varieties ('FFT-52' and 'KB-2010') were each inoculated in a culture medium, and cultured at a room temperature (20° C.) for 40 days. Thereafter, the culture medium in which mycelia were fully propagated was taken out of the culture bag, and the mycelia in the culture medium was further cultured for 60 days. Thus, a fungal bed was prepared. Then, a plurality of such fungal beds of the aforementioned varieties were cultivated to be allowed to develop fruit bodies. During a mycelium propagation period before the 40th day of culturing, side surfaces of a culture container were covered with an aluminum vapor-deposited heat-insulating sheet so as not to release heat generated by the mycelia.

With the culture container thus surrounded with the heat-insulating sheet, the culture medium was maintained at a temperature of not lower than 27° C. for 9 days and at a temperature of not lower than 28° C. and lower than 29.5° C. for 5 days in the 40-day mycelium propagation period. Thus, the culture medium in which the mycelia were propagated was subjected to a high-temperature load.

In general, the temperature of the culture medium rises as the amount of the mycelia increases in the mycelium propagation period, and the heat generation is at its peak on around the 14th to 21st culture days. Shiitake mushrooms are generally vulnerable to heat, and shiitake mushroom mycelia per se are weakened or damaged in a temperature range not lower than 26° C. Therefore, the room temperature should be controlled so as to maintain the temperature of the culture medium at lower than 26° C. at the highest.

During the high-temperature load period, the color of a mycelium growing zone of the culture medium in which 'KB-2010' was cultured was not changed to yellow in 75% of the culture medium, and the fungal bed of the unyellowed culture medium rotted during the subsequent culture and cultivation (see FIG. 21). Therefore, normal fruit bodies of 'KB-2010' were harvested at a lower crop yield.

In contrast, the fungal bed of 'FFT-52' was thereafter properly cultured and cultivated without any apparent problems (see FIG. 22).

[Dual Culture]

Dual culture was performed based on Research Report on Plant Variety Characteristic Classification, Mushroom (shiitake), 1994-1995, Japan by culturing 'FFT-52' and 12 commercially available varieties on potato dextrose agar (PDA) media (see FIGS. 23A to 35B). The results of the dual culture are shown below in Table 6. In Table 6, the mark "+" indicates that an inhibition zone was formed in the dual culture, and the mark "−" indicates that the inhibition zone was not formed in the dual culture.

TABLE 6

(Results of dual culture of 'FFT-52')

| | |
|---|---|
| FFT-52 | − |
| FFT-52 | − |
| KA-1001 | + |
| H600 | + |
| KB-2010 | + |
| KV-92 | + |
| 9K-4 | + |
| XR1 | + |
| XR18 | + |
| ML8 | + |
| A-567 | + |
| K241 | + |
| H607 | + |
| KX-S055 | + |

As shown above in Table 6, the inhibition zone (antagonistic line) was formed between 'FFT-52' and each of the 12 commercially available varieties. Thus, it was confirmed that 'FFT-52' is genetically different from the 12 commercially available varieties.

What is claimed is:

1. A new and distinct variety of shiitake mushroom plant named 'FFT-52' as substantially illustrated and described herein.

* * * * *

【FIG.1】
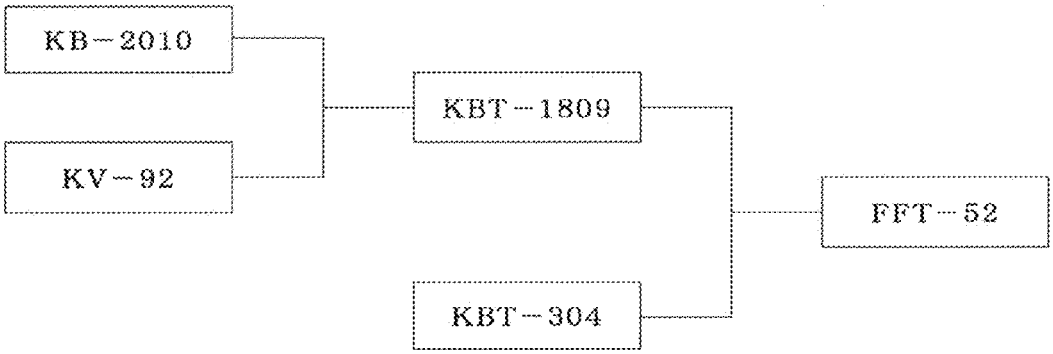
【FIG.2】
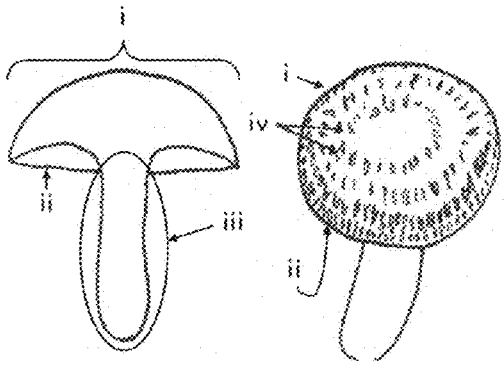
【FIG.3】
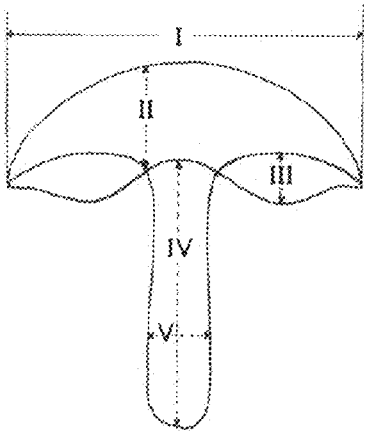

【FIG.4A】
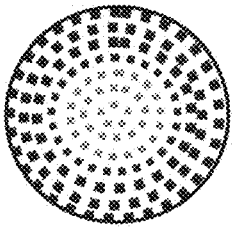
【FIG.4B】
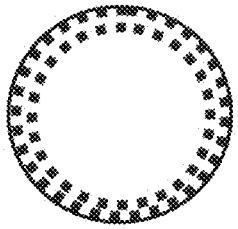
【FIG.4C】
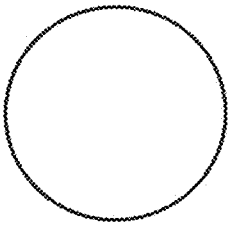
【FIG.5A】
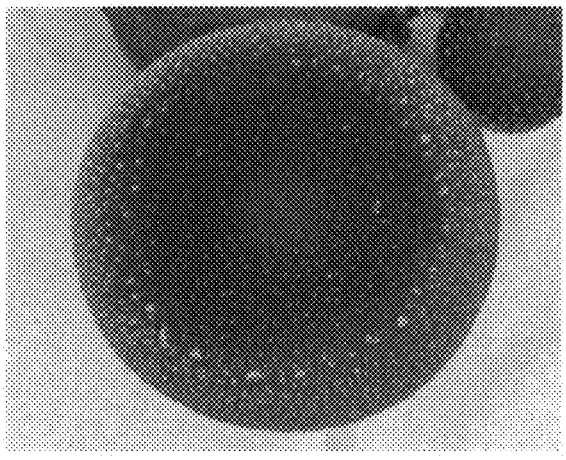

【FIG.5B】
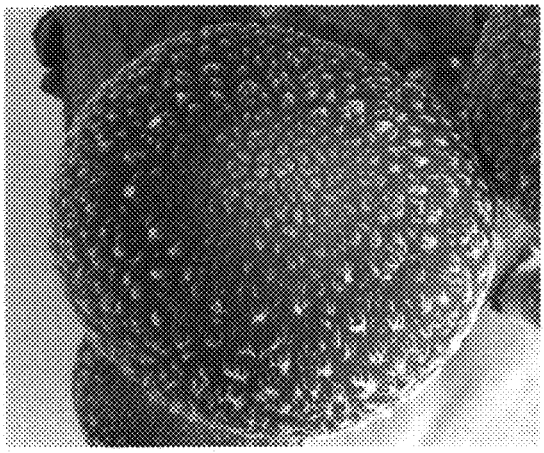
【FIG.5C】
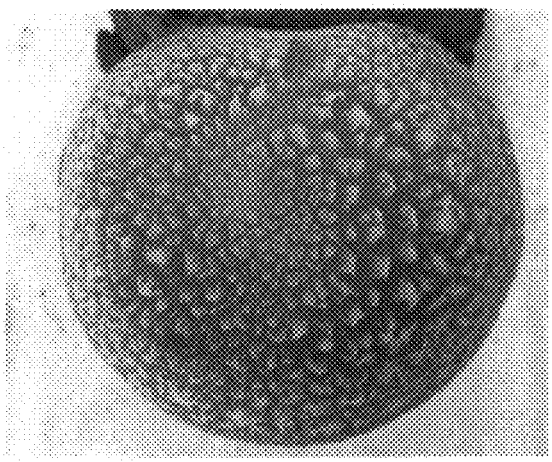
【FIG.6A】
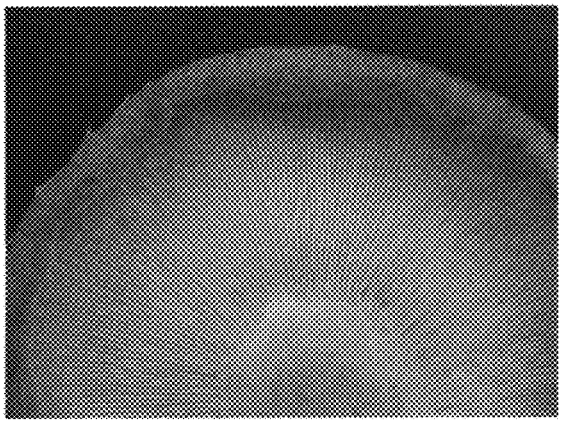

【FIG.6B】
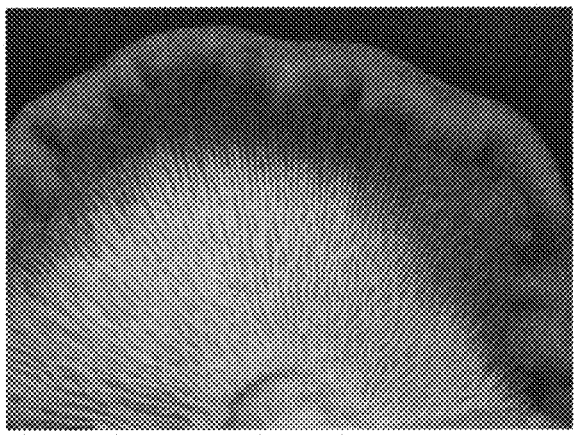
【FIG.7A】
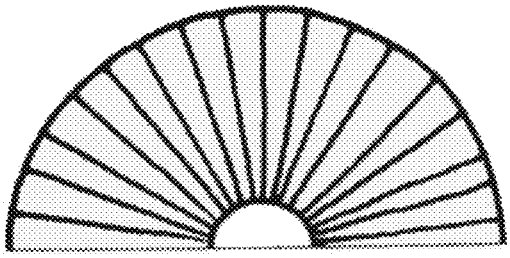
【FIG.7B】
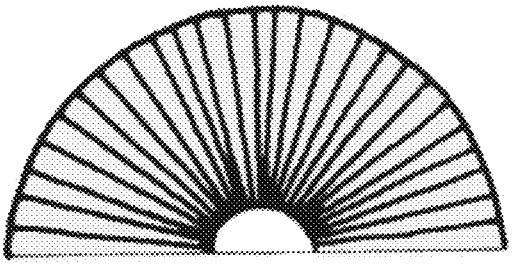

【FIG.8】
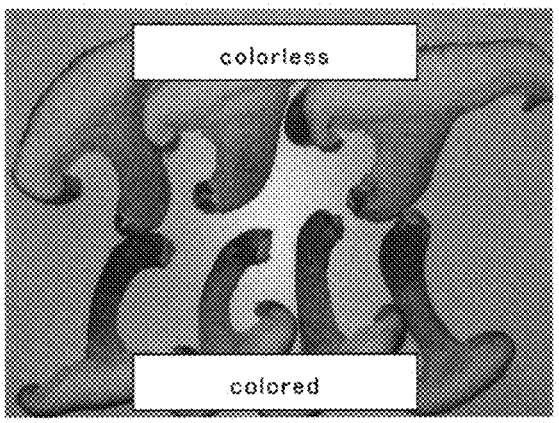
【FIG.9】
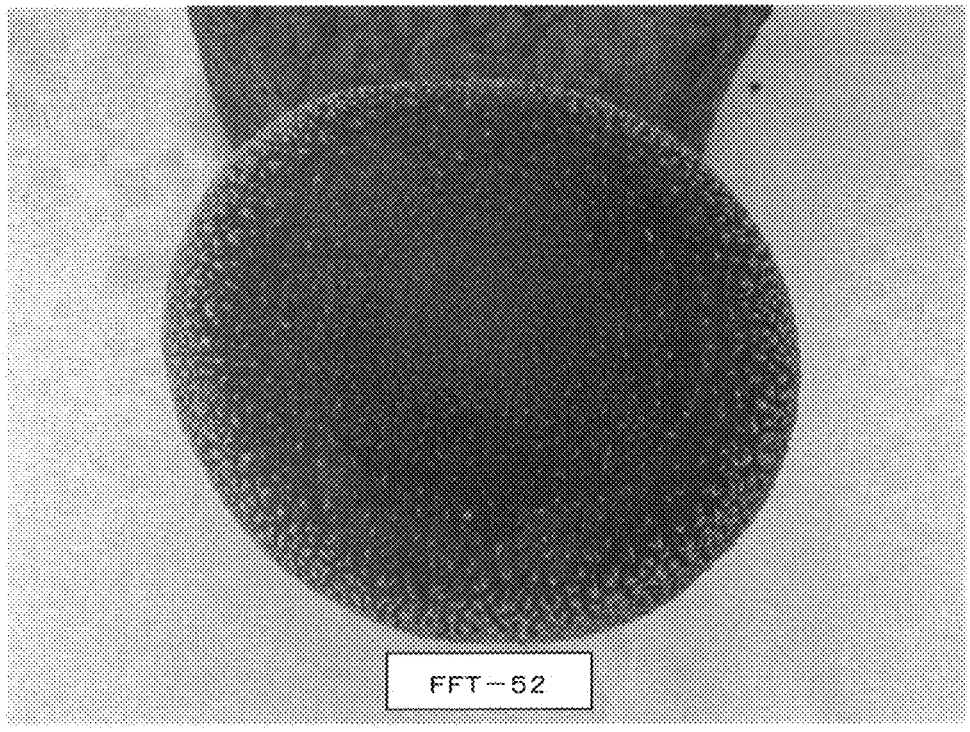

【FIG.10】
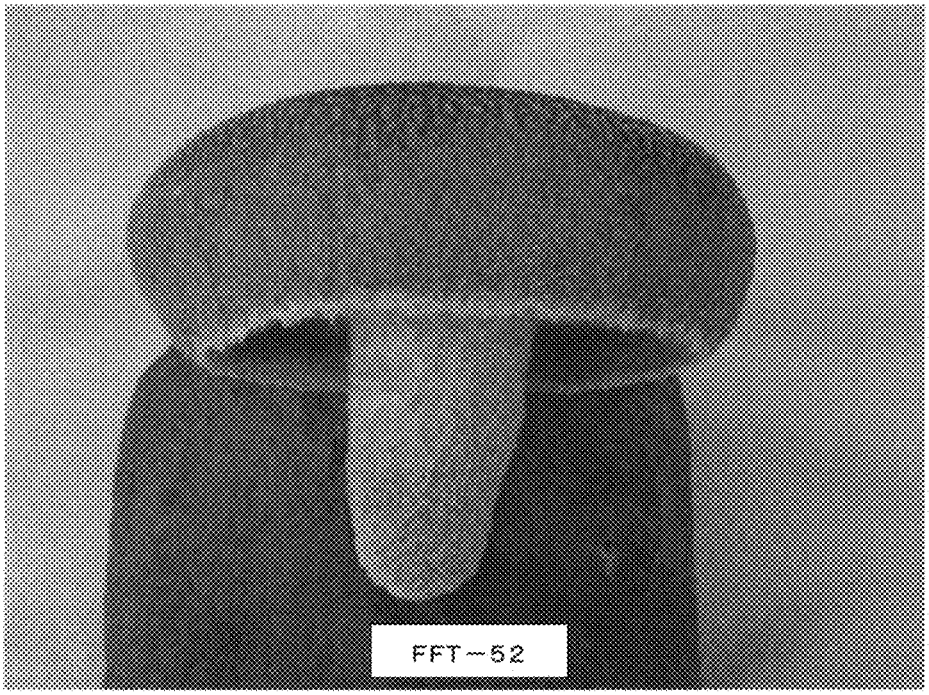
【FIG.11】
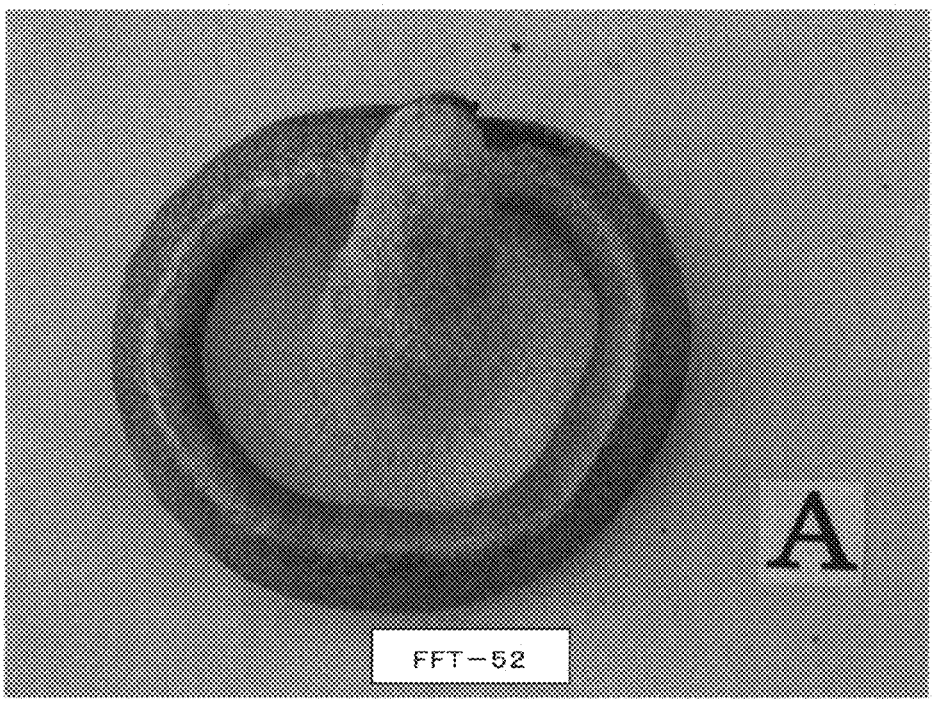

【FIG.12】
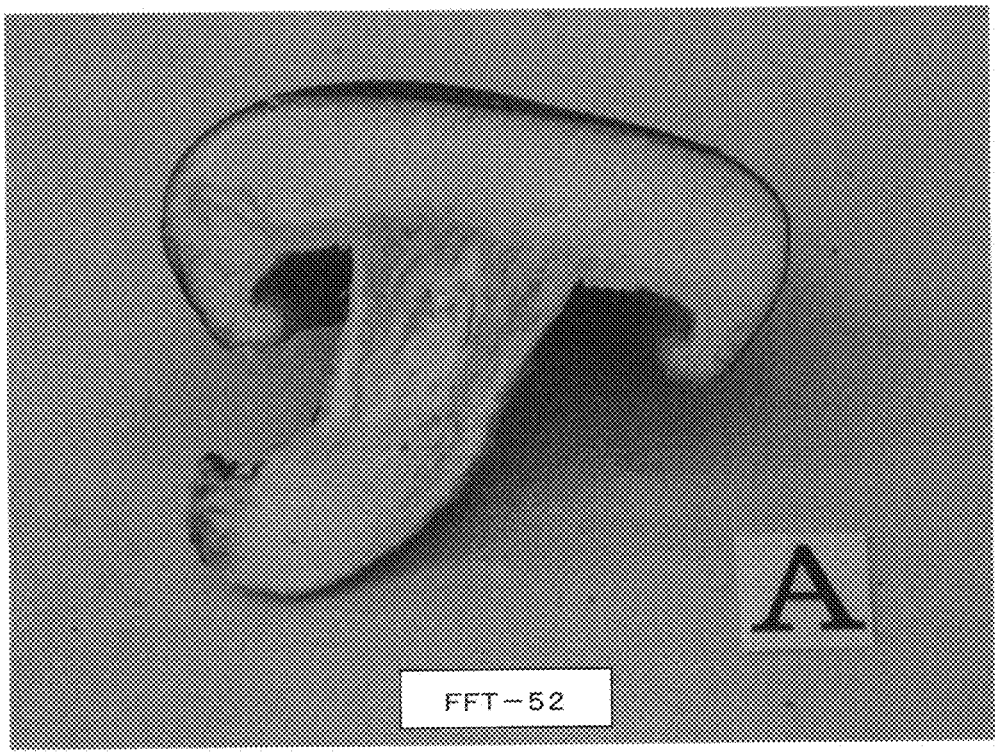
【FIG.13】
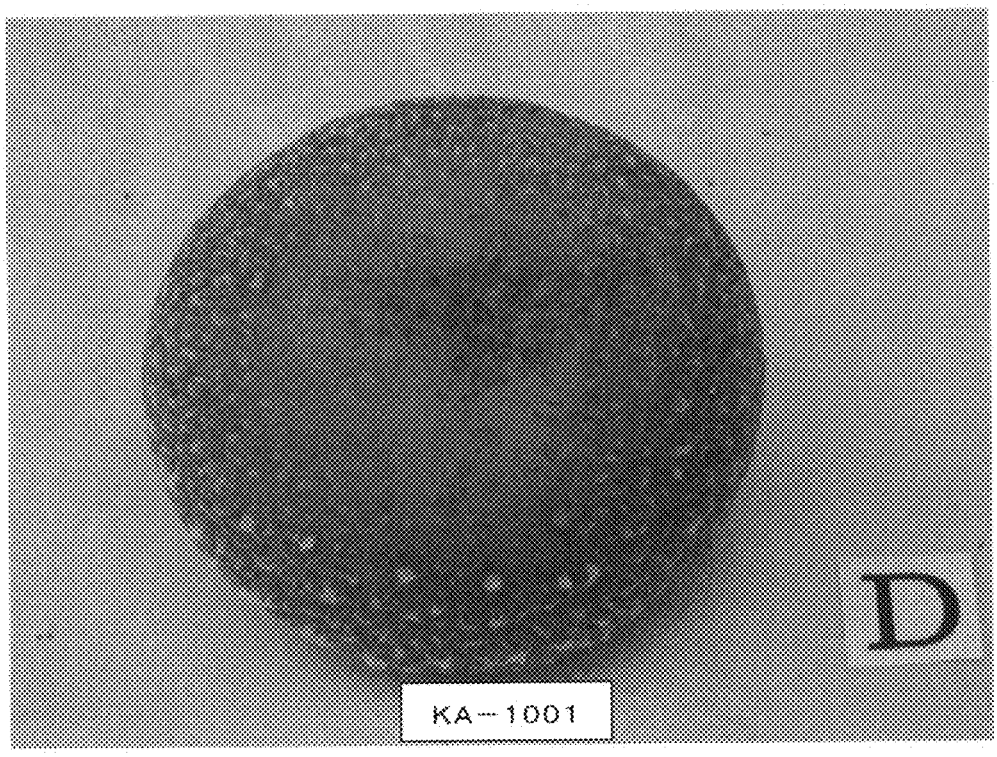

【FIG.14】
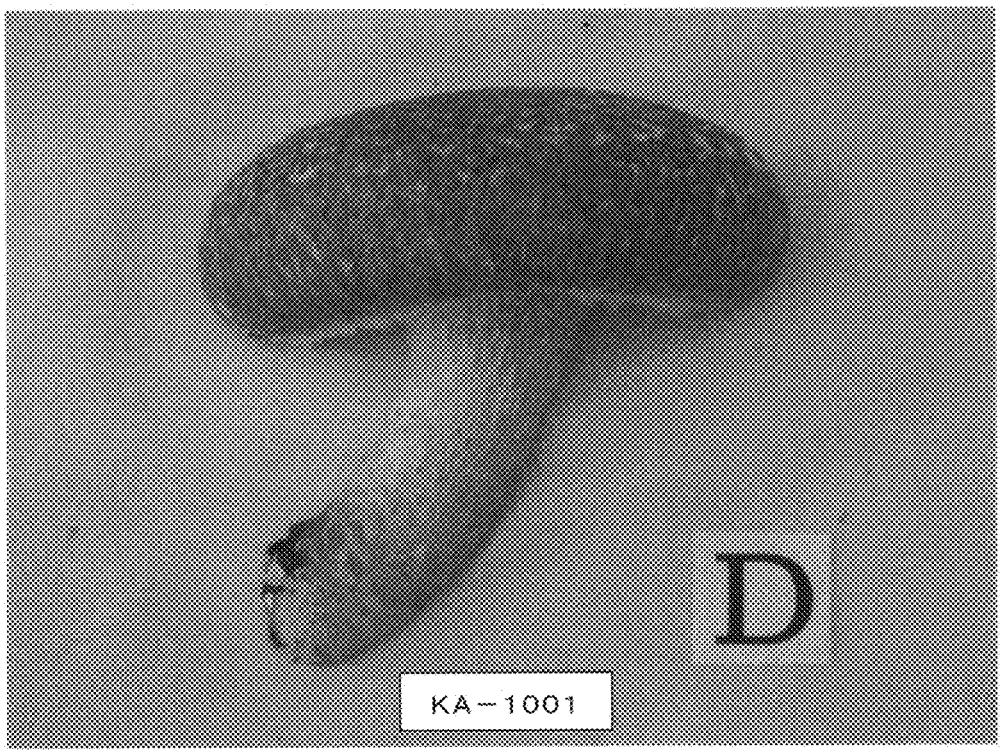
【FIG.15】
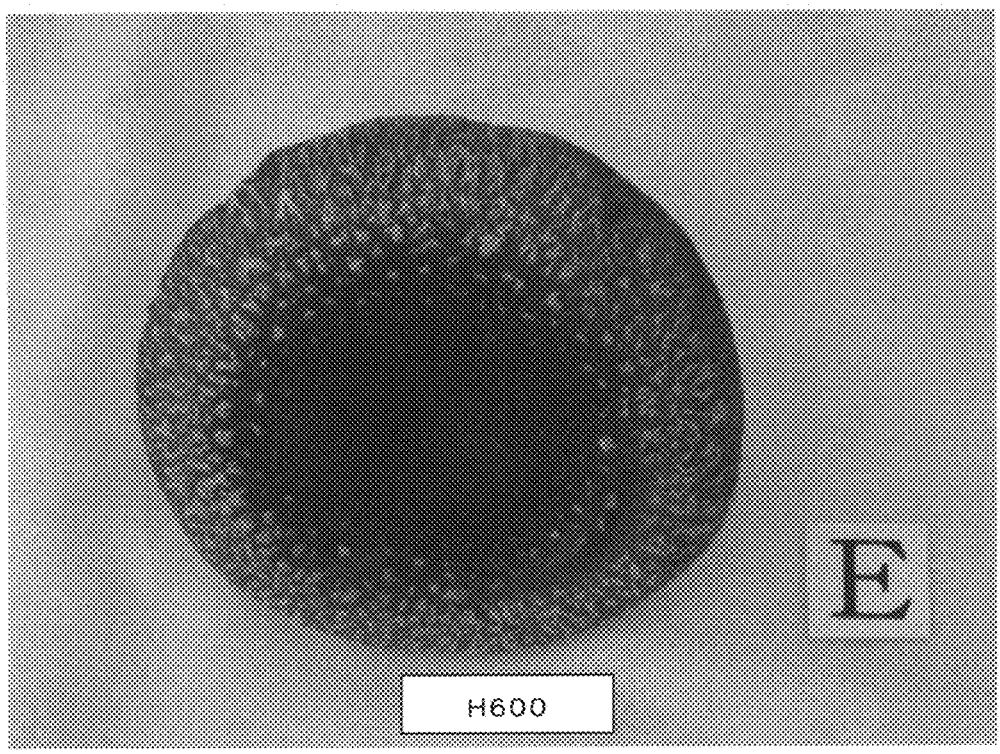

【FIG.16】
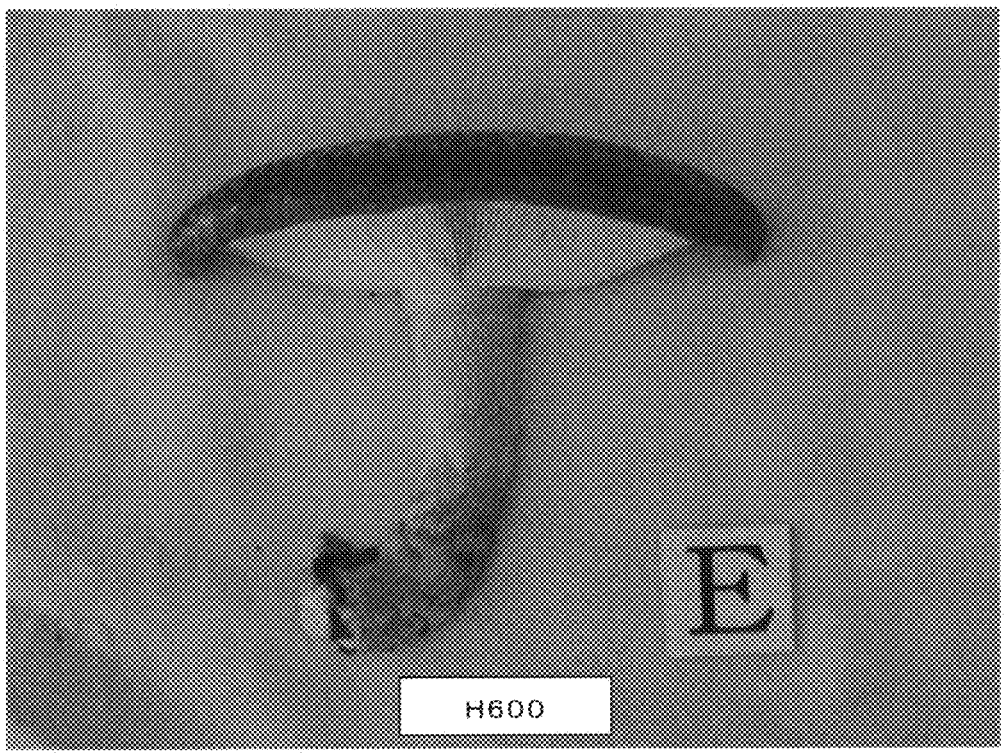
【FIG.17】
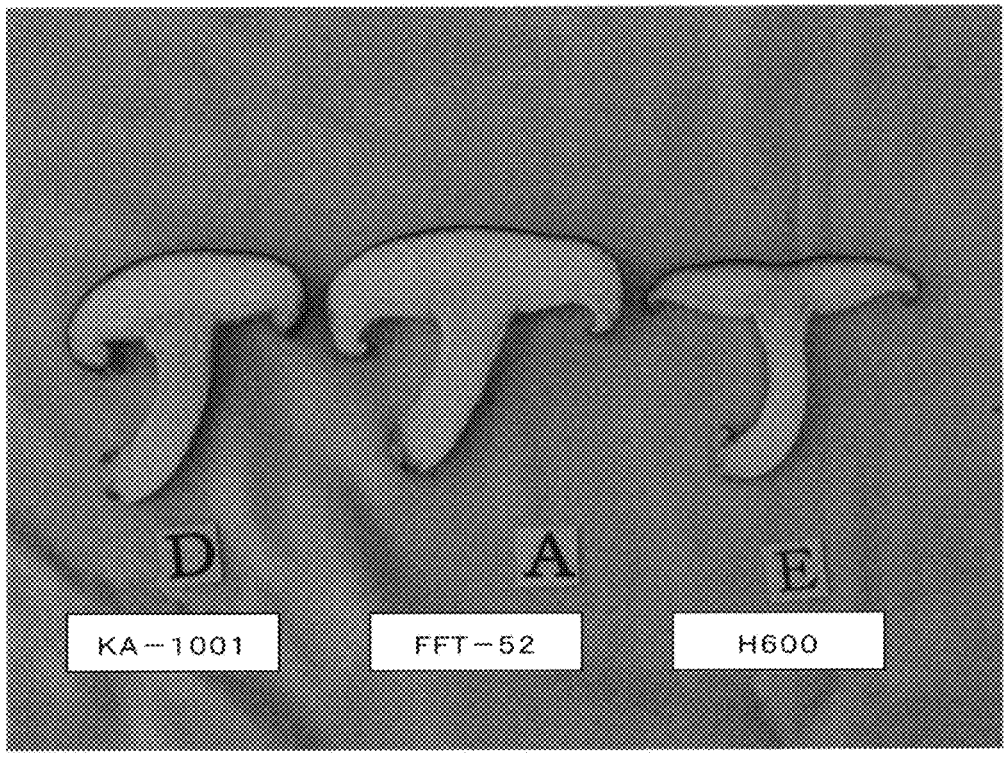

【FIG.18】
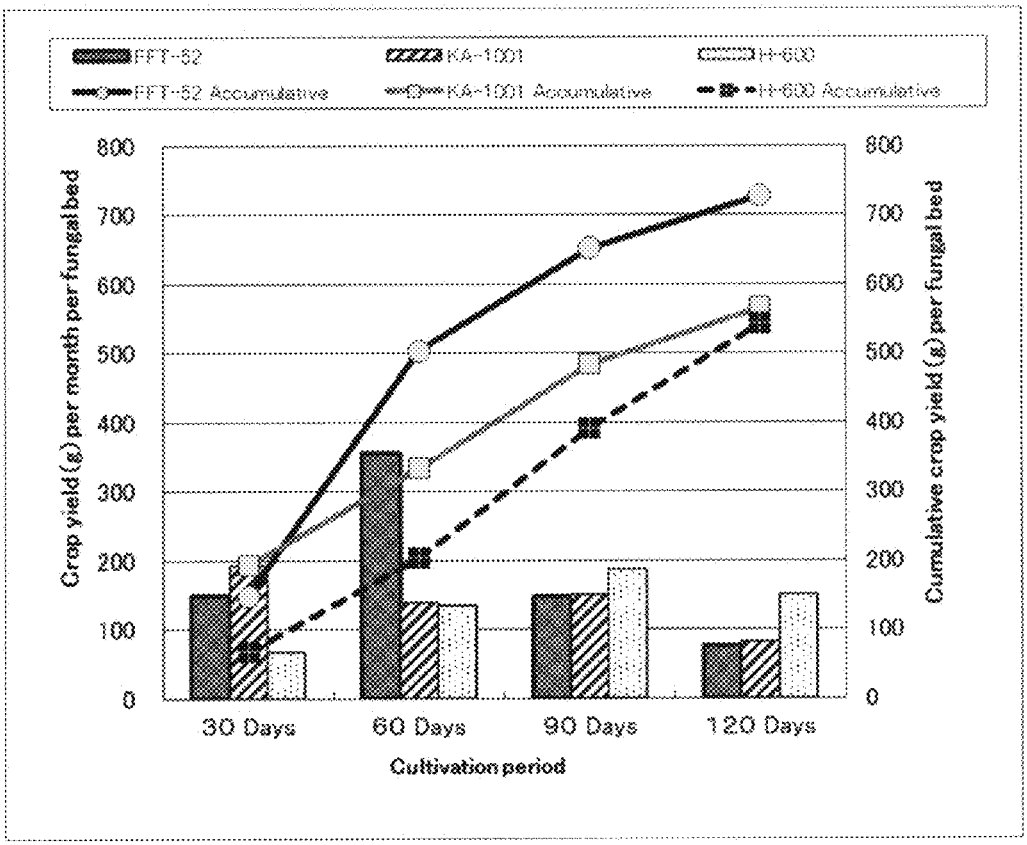

【FIG.19】
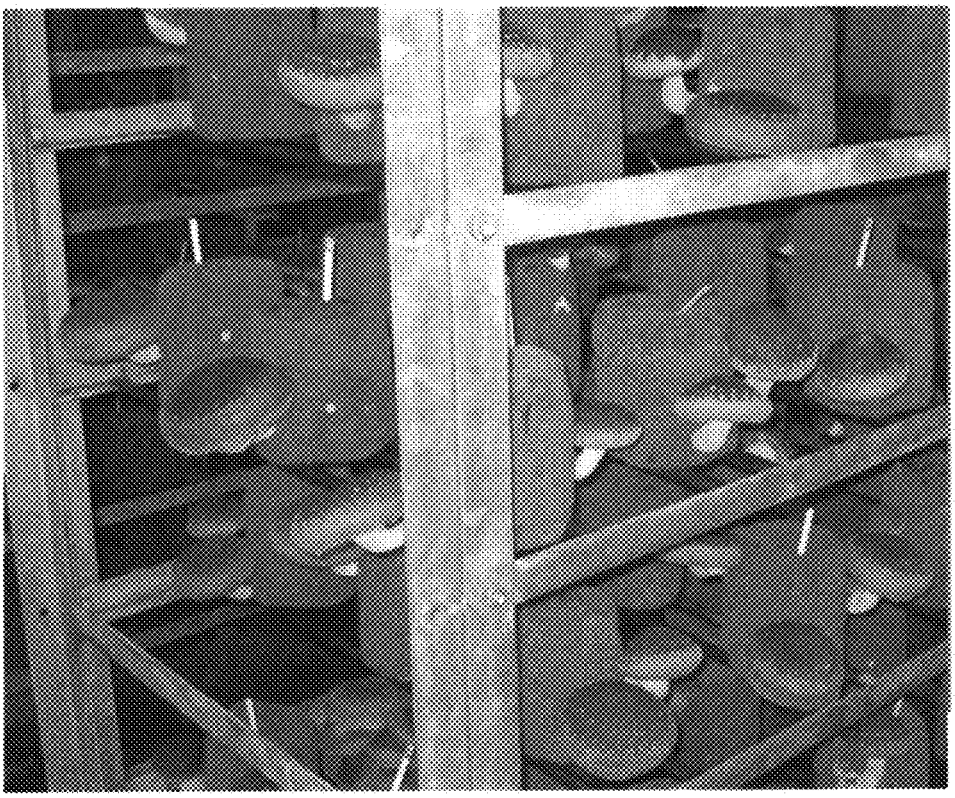
【FIG.20】
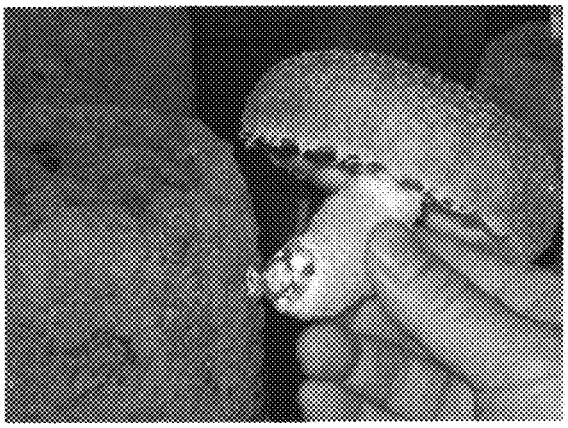

【FIG.21】
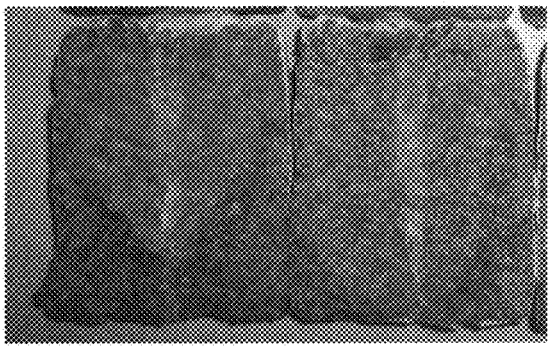
【FIG.22】
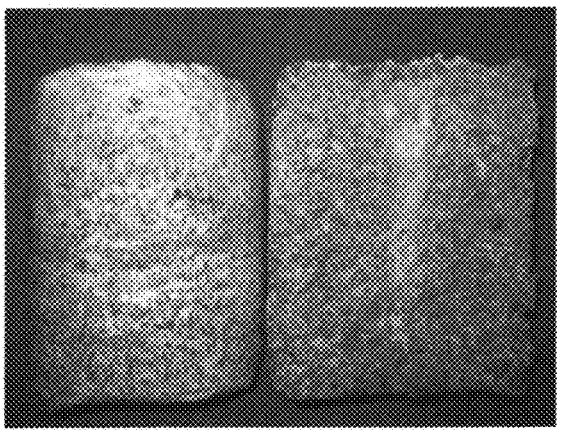

【FIG.23A】
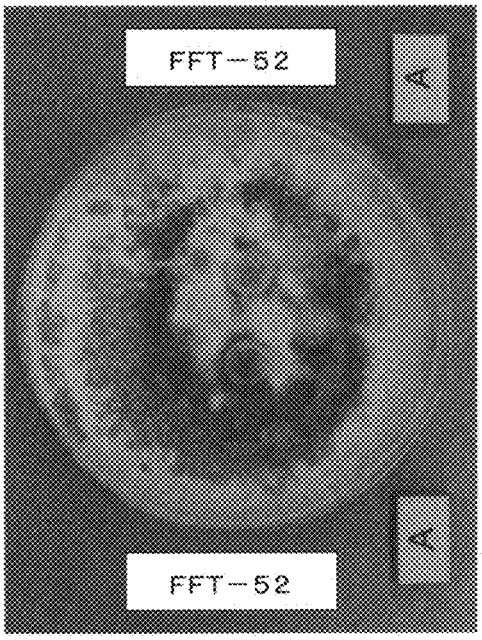
【FIG.23B】
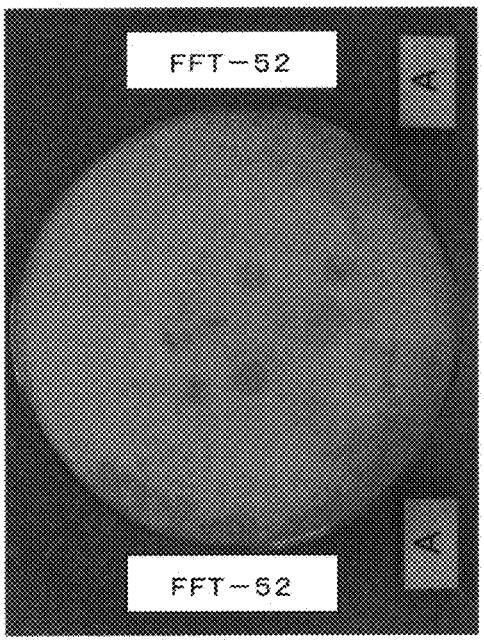

【FIG.24A】
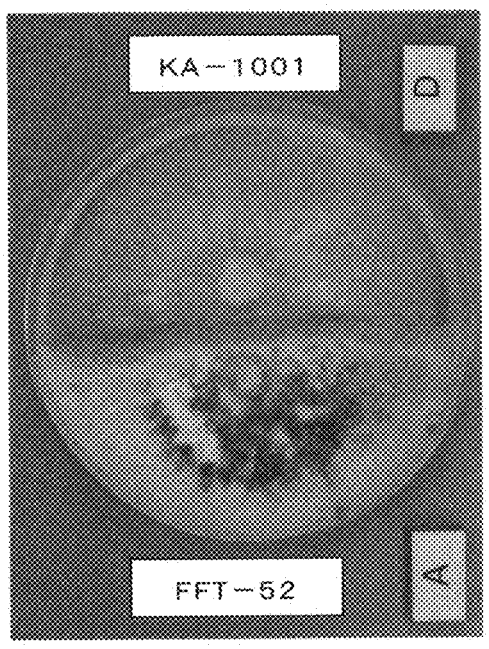
【FIG.24B】
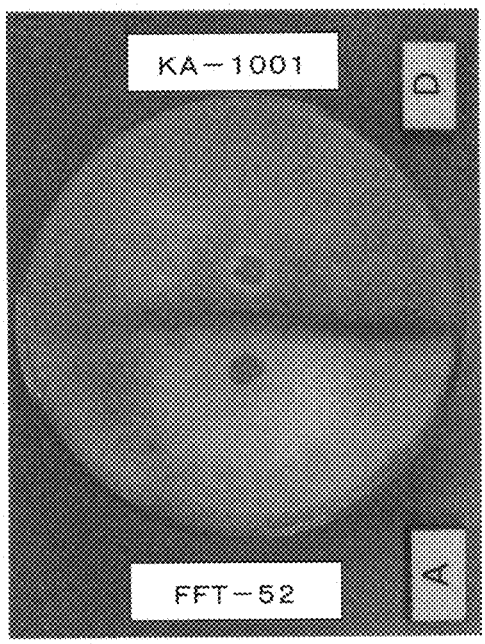

【FIG.25A】
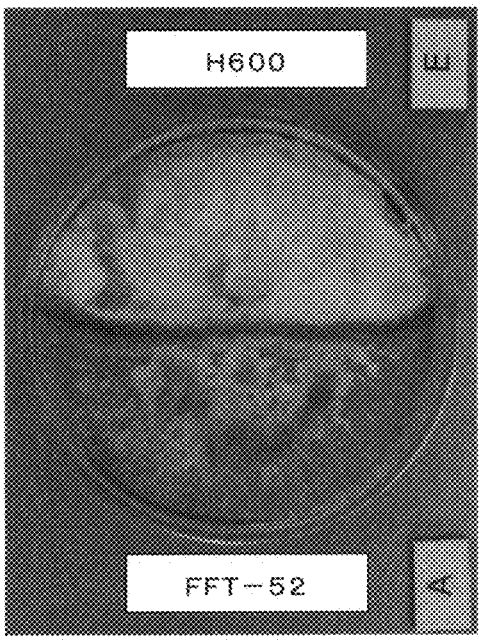
【FIG.25B】
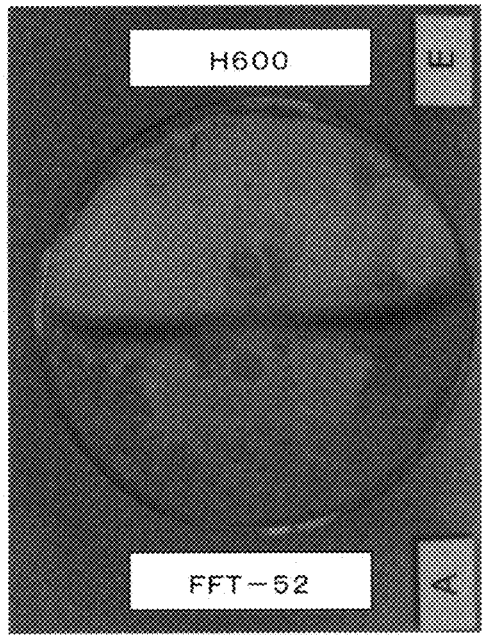

【FIG.26A】
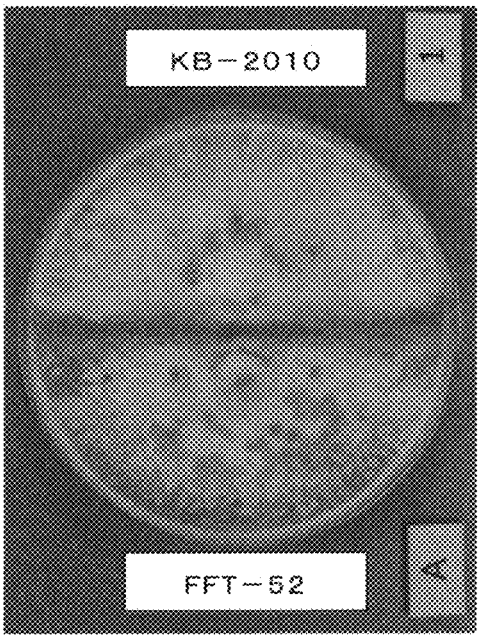
【FIG.26B】
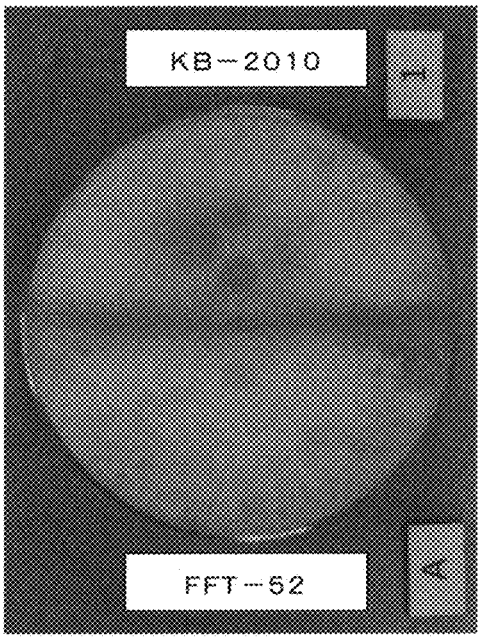

【FIG.27A】
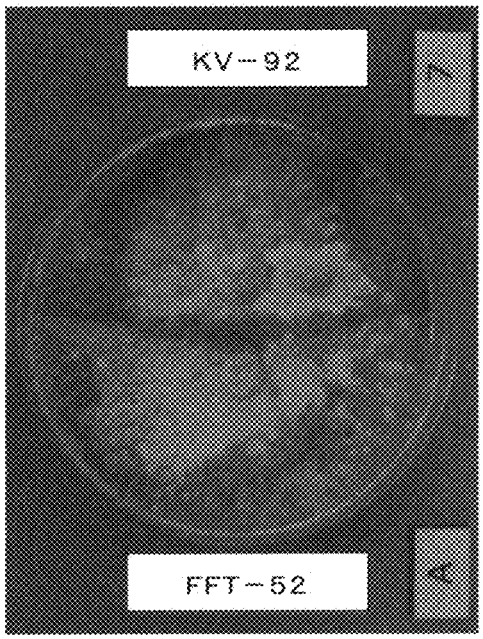
【FIG.27B】
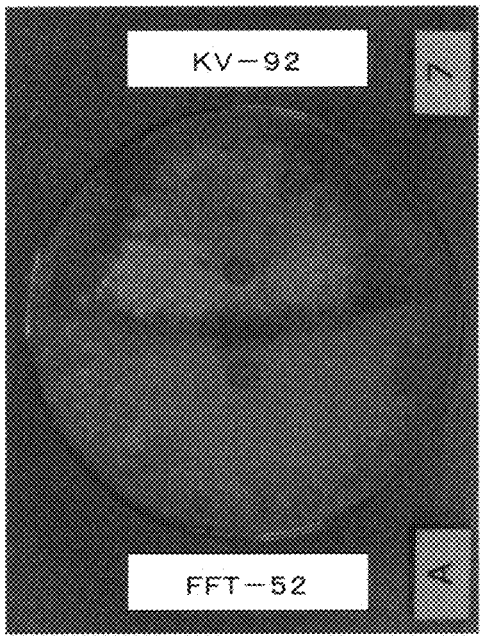

【FIG.28A】
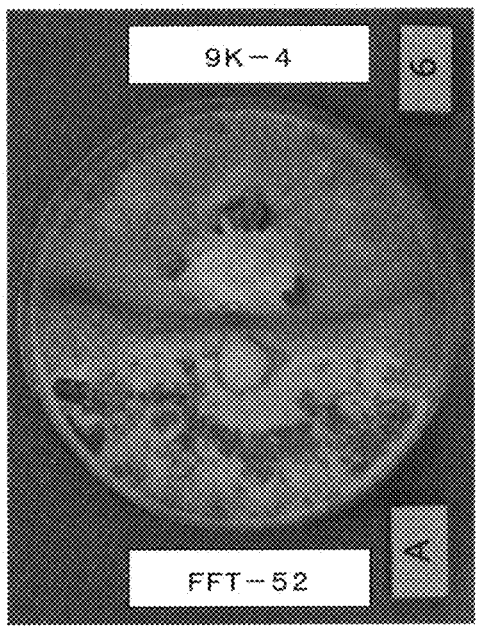
【FIG.28B】
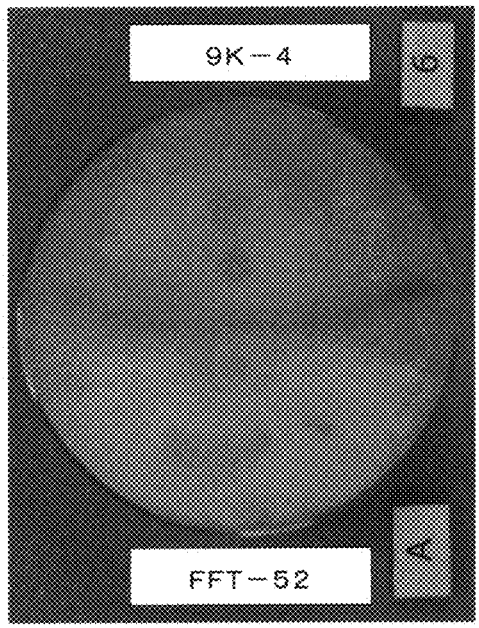

【FIG.29A】
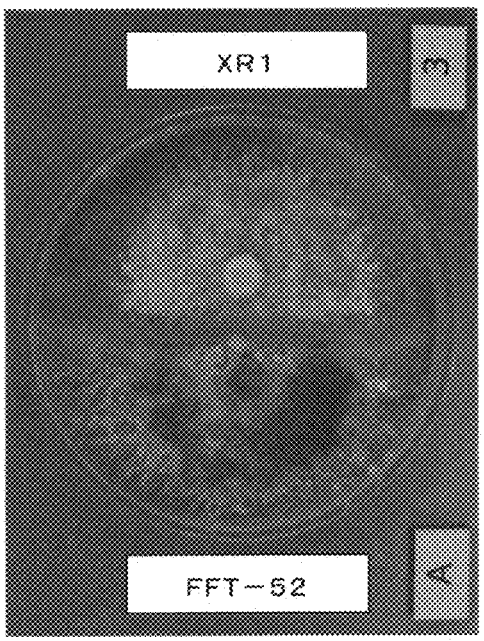
【FIG.29B】
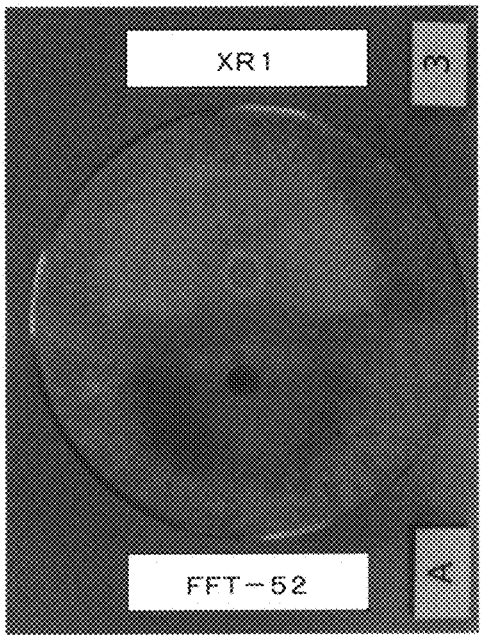

【FIG.30A】
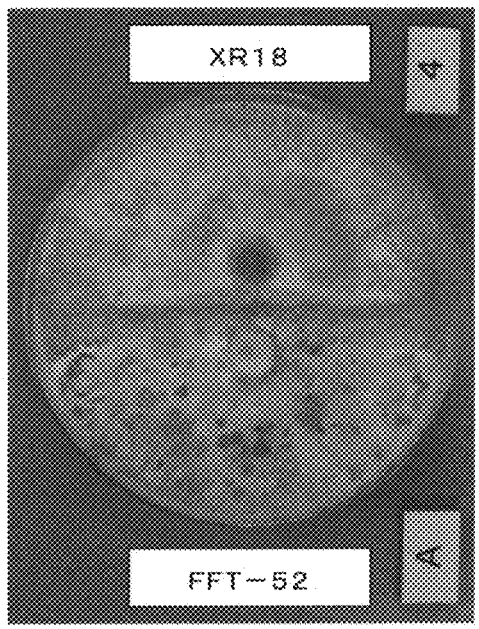
【FIG.30B】
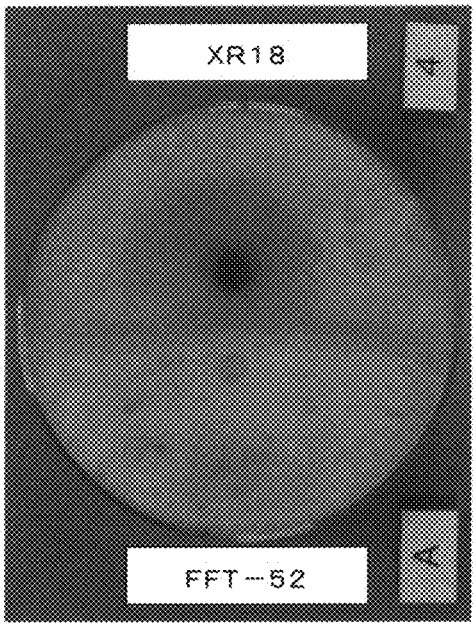

【FIG.31A】
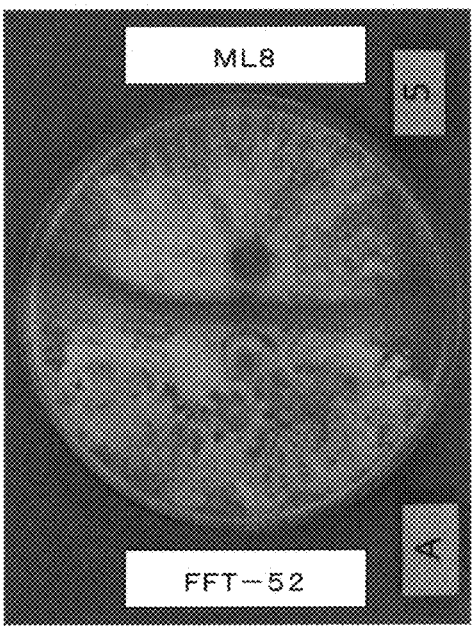
【FIG.31B】
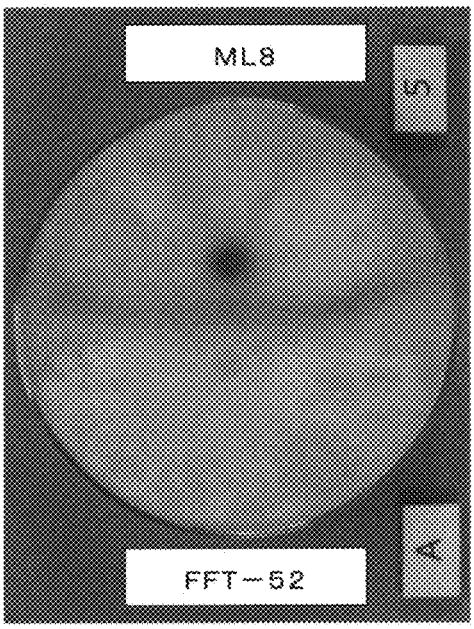

【FIG.32A】
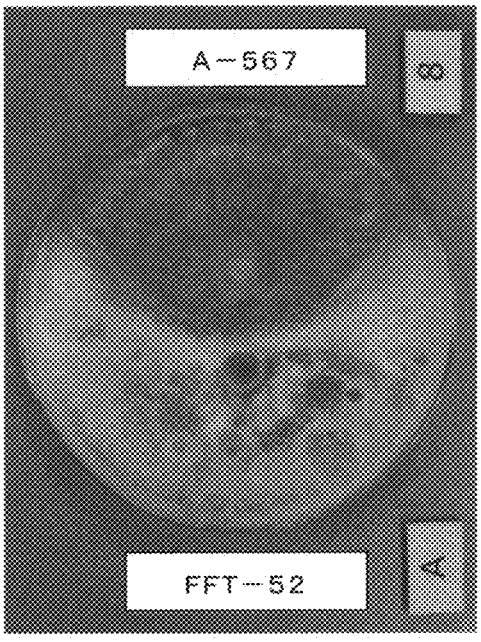
【FIG.32B】
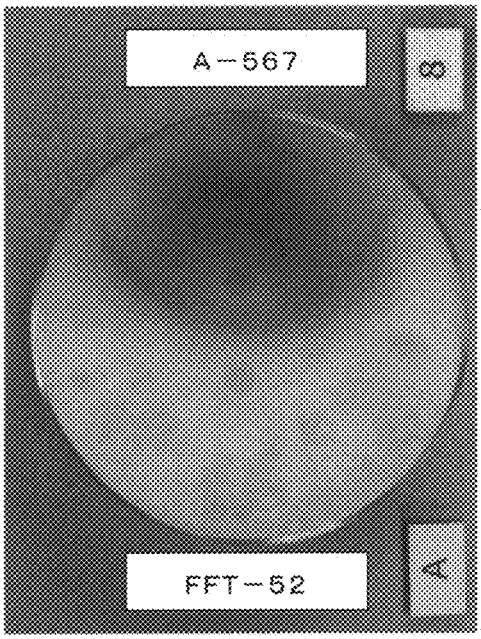

【FIG.33A】
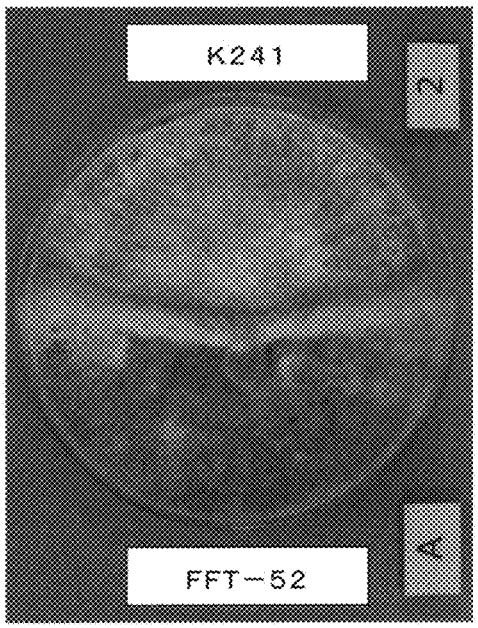
【FIG.33B】
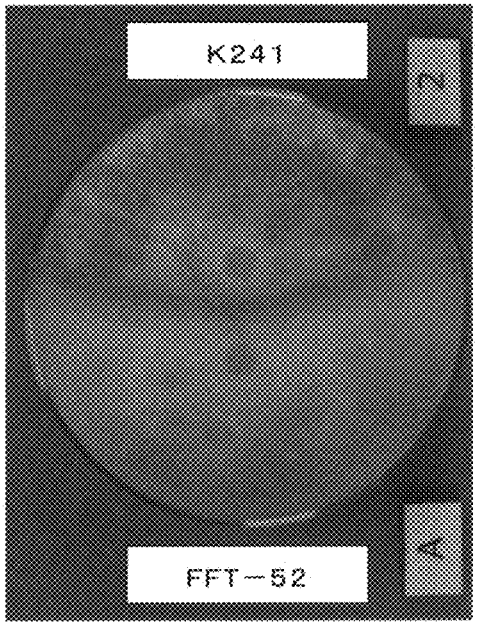

【FIG.34A】
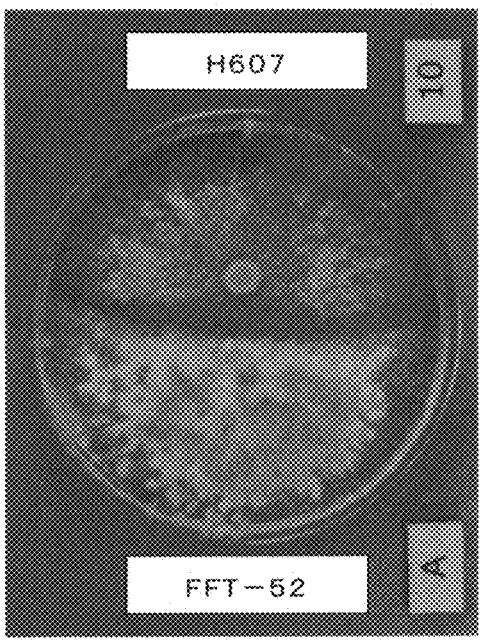
【FIG.34B】
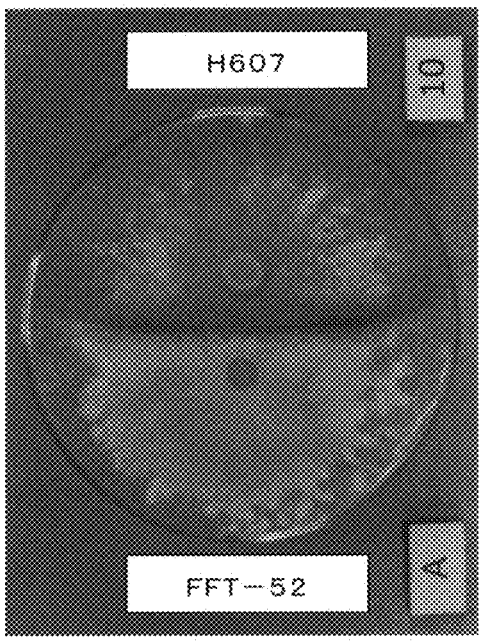

【FIG.35A】
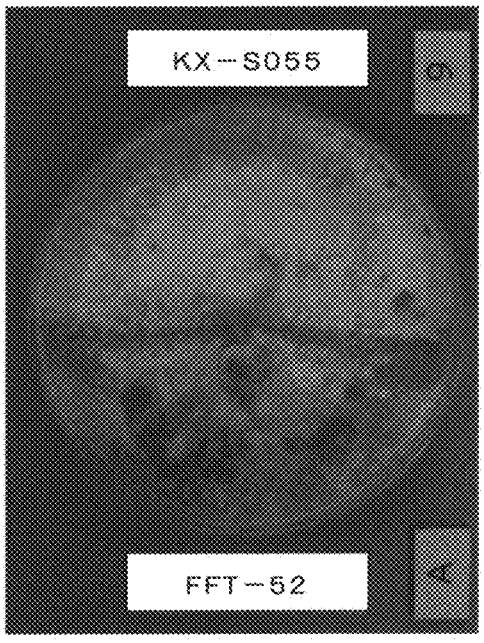
【FIG.35B】
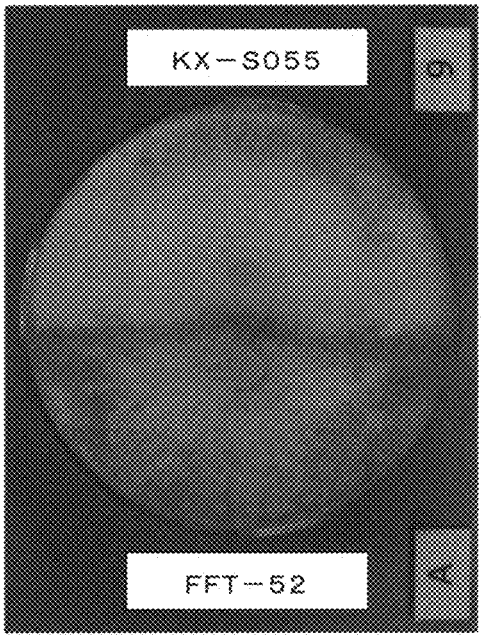

FIG. 36

(Observation of shape of pileus)

| | | FFT-52 | KA-1001 | H600 |
|---|---|---|---|---|
| Shape of Pileus | | | | |
| Plan view of pileus (as viewed from top) | Round | 100 | 100 | 100 |
| | Fan-shape | 0 | 0 | 0 |
| Side view of pileus (as viewed from lateral side) | Concave | 0 | 0 | 0 |
| | Flat | 63 | 61 | 10 |
| | Convex | 37 | 39 | 90 |
| | Umbonate | 0 | 0 | 0 |
| | Other shape | 0 | 0 | 0 |
| Section of pileus (taken through center of pileus) | 1 | 44 | 97 | 34 |
| | 2 | 0 | 0 | 66 |
| | 3 | 56 | 3 | 0 |
| | 4 | 0 | 0 | 0 |
| | 5 | 0 | 0 | 0 |

FIG. 37

(Observation of hymenophore)

| Hymenophore | | FFT-52 | KA-1001 | H600 |
|---|---|---|---|---|
| Shape | Triangle apart from stipe | 89 | 95 | 94 |
| | Triangle attached to stipe | 11 | 5 | 5 |
| | Earlobe | 0 | 0 | 1 |
| | Round tip | 0 | 0 | 0 |
| | Incised | 0 | 0 | 0 |
| Gill configuration | Normal | 63 | 83 | 90 |
| | Wavy | 37 | 17 | 10 |
| Density | Sparse | 0 | 0 | 0 |
| | Intermediate | 100 | 100 | 100 |
| | Dense | 0 | 0 | 0 |
| Color | Yellowish white (RHS NN155A) | 100 | 100 | 100 |
| | Pale Yellow (RHS 158B) | 0 | 0 | 0 |
| | Moderate orange yellow (RHS 164B) | 0 | 0 | 0 |
| | Moderate orange (RHS 166D) | 0 | 0 | 0 |

FIG. 38

(Observation and evaluation of stipe)

| Stipe | | FFT-52 | KA-1001 | H600 |
|---|---|---|---|---|
| Shape | Cylindrical shape | 41 | 36 | 32 |
| | Upwardly enlarged shape | 57 | 62 | 18 |
| | Barrel shape | 2 | 2 | 50 |
| Color | Colorless | 100 | 100 | 0 |
| | Colored | 0 | 0 | 100 |
| Fluff | Absent | 0 | 0 | 0 |
| | Present | 100 | 100 | 100 |
| Flesh texture (Hardness determined by pinching stipe with fingers) | Soft (equivalent to JMS7H-3) | 0 | 0 | 2 |
| | Intermediate | 24 | 67 | 63 |
| | Hard (equivalent to KINKO 535) | 76 | 33 | 35 |